United States Patent [19]

Stoyan

[11] Patent Number: 4,952,045
[45] Date of Patent: Aug. 28, 1990

[54] CORNEAL CONTACT LENS AND METHOD FOR TREATING MYOPIA

[76] Inventor: Nick Stoyan, 3841 Diamante Pl., Encino, Calif. 91436

[21] Appl. No.: 357,365

[22] Filed: May 26, 1989

[51] Int. Cl.⁵ .............................................. G02C 7/04
[52] U.S. Cl. ........................... 351/160 R; 351/160 H; 351/177
[58] Field of Search ............... 351/160 R, 160 H, 161, 351/162, 177

[56] References Cited

U.S. PATENT DOCUMENTS

| | | | |
|---|---|---|---|
| 3,831,604 | 8/1974 | Neefe | 351/160 R |
| 4,418,991 | 12/1983 | Breger | 351/161 |
| 4,525,043 | 6/1985 | Bronstein | 351/160 R |

*Primary Examiner*—Scott J. Sugarman
*Attorney, Agent, or Firm*—Poms, Smith, Lande & Rose

[57] ABSTRACT

A corneal contact lens for use in treating myopia by controlled corneal molding. The lens includes a central zone having a central zone radius of curvature and a tear zone located concentrically around the central zone. The tear zone is integral with the central zone and has a radius of curvature which is smaller than the central zone. The lens may also include a peripheral zone located concentrically around the tear zone wherein the peripheral zone has a radius of curvature equal to or greater than the central zone.

16 Claims, 1 Drawing Sheet

4,952,045

CORNEAL CONTACT LENS AND METHOD FOR TREATING MYOPIA

BACKGROUND OF THE INVENTION

1. Field of the Invention

The present invention relates generally to corneal contact lens and their use in treating myopia. More particularly, the present invention involves a corneal contact lens which is shaped to provide altering of the patient's cornea during continued wear in a manner which reduces the myopic condition.

2. Description of Related Art

Myopia, also known as nearsightedness, is a condition where the radius of curvature of the cornea is smaller than normal. Individuals with this condition have difficulty in focusing on distant objects because the cornea is curved too sharply to provide adequate focusing. Myopia is a common condition for which no entirely suitable permanent treatment has been developed.

One approach to correcting myopia is through surgical reshaping of the cornea. However, such surgical procedures have not been entirely proven and there is some question as to the permanency of the surgically altered lens shape. Another approach is to alter the corneal shape by wearing corneal contact lenses which are designed to continually bias or exert pressure on the cornea to gradually force or mold the cornea into the desired normal corneal curvature. A retainer lens is then worn on a part-time basis to prevent the cornea from returning to its original shape. This method of treatment is commonly referred to as orthokeratology.

The success of any treatment by orthokeratology is dependent upon the shape and structure of the corneal contact lens. There presently is a need to provide lens shapes which are useful in promoting relatively rapid and safe reshaping of the myopic cornea. Further, such corneal contact lenses must be comfortable to wear and provide acceptable vision correction during the cornea reshaping process.

SUMMARY OF THE INVENTION

In accordance with the present invention, a corneal contact lens is disclosed which is useful in changing the radius of curvature and shape of the myopic cornea into the desired configuration for normal vision. The lens of the present invention includes a central zone and tear zone located concentrically around the central zone. The two zones are integral with each other and the radius of curvature of the tear zone is smaller than the central zone. It was discovered that such a corneal contact lens shape is useful in changing the shape of the myopic cornea to that of a normally shaped cornea. The sharper curve of the tear zone provides a ring shaped area where tear fluid is concentrated between the lens and cornea. It also provides for reshaping or molding of the myopic cornea to reduce curvature and improve vision.

As a feature of the present invention, the corneal contact lens may also include a peripheral zone which is located concentrically around and integral with the tear zone. The peripheral zone has a radius of curvature which is greater than or equal to the radius of curvature of the central zone. In addition, the various dimensions of the lenses are designed to promote desired changes in the shape of the myopic cornea. As another feature of the present invention, the tear zone portion of the lens is laterally thinner than the central zone or peripheral zone. This configuration is especially well suited for promoting change of the myopic cornea toward the normally shaped cornea.

The above discussed and many other features and attendant advantages of the present invention will become better understood by reference to the following detailed description when viewed in conjunction with the accompanying drawings.

DETAILED DESCRIPTION OF THE PREFERRED EXEMPLARY EMBODIMENTS

Figure 1:
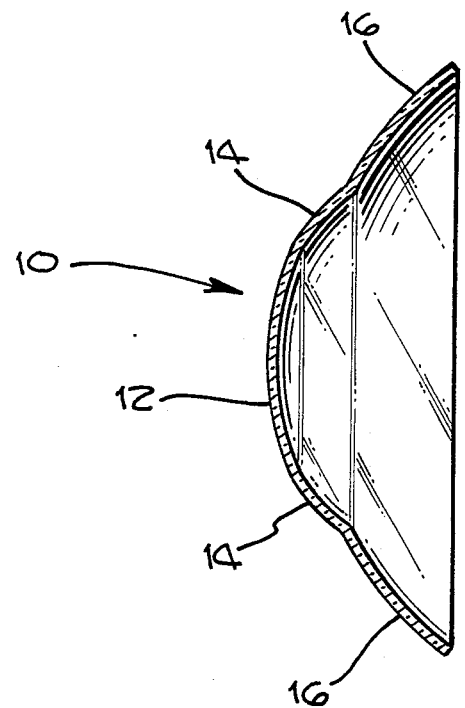
FIG. 1 is a sectional side view of a preferred exemplary corneal contact lens in accordance with the present invention.
Figure 2:
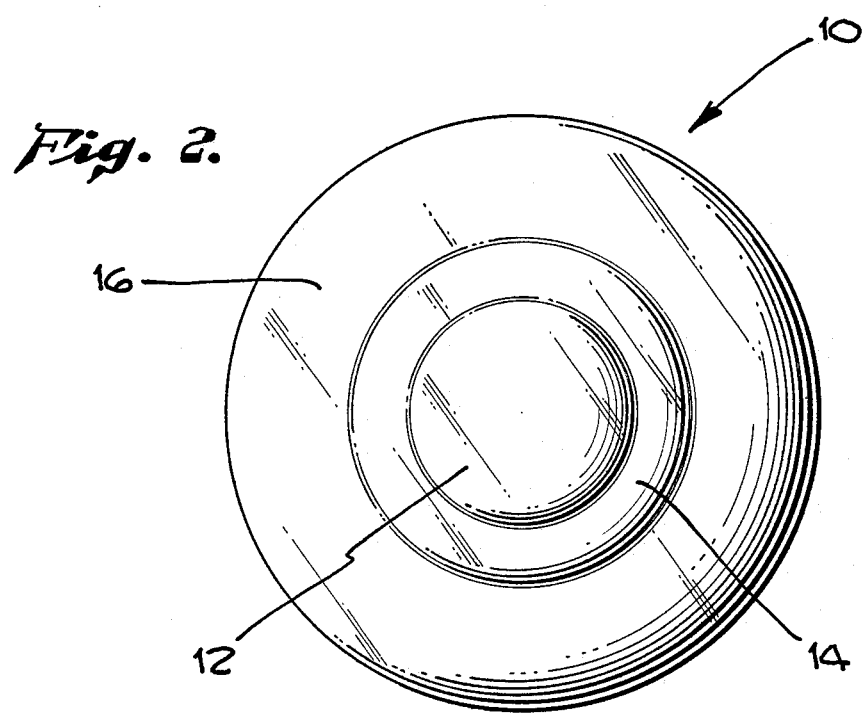
FIG. 2 is a front view of the preferred exemplary lens shown in FIG. 1.

A preferred exemplary corneal contact lens in accordance with the present invention is shown generally at 10 in FIGS. 1 and 2. The lens 10 includes a central portion or zone 12, a tear portion or zone 14, and a peripheral portion or zone 16. The overall dimensions of the lens 10 are within the normal ranges for corneal contact lenses. The outside diameter of the lens 10 is typically between about 5 to 20 millimeters with other diameters being possible in special cases. The lens has a lateral or cross-sectional thickness of between about 0.05 millimeters to 10 millimeters. Thicknesses in the range of 0.05 to 0.5 millimeters are preferred.

The central zone 12 has a radius of curvature of between about 4 to 20 millimeters. The diameter of the central zone 12 is between about 2-12 millimeters. Preferred ranges for the radius of curvature and diameter are 7 to 10 millimeters and 4 to 8 millimeters, respectively. The tear zone 14 is integral with the central zone 12 in that the lens 10 is machined or molded from a single piece of plastic. The tear zone 14 forms a ring around the central zone 12. The radial thickness of the tear zone ring 14 is between about 0.2 to 10 millimeters. The radius of curvature of the tear zone 14 is between about 0.1 to 12 millimeters. The preferred ranges are from 0.2 to 5 millimeters for the radial thickness and 7 to 10 millimeters for the radius of curvature.

As an important aspect of the present invention, the radius of curvature of the tear zone 14 must be smaller than the radius of curvature for the central zone 12. This creates a zone of increased curvature around the central zone which provides desirable reshaping of the cornea. In addition, a circular tear channel or duct is formed between the tear zone 14 and the eye to provide a concentrated circular zone or reservoir of tear fluid which helps position the lens centrally on the cornea and enhances lens wearing comfort.

Although not essential, it is preferred that the lateral thickness of the tear zone 14 be less than that of the central zone 12. This increases the reshaping effect of the lens on the cornea and also increases the size of the tear duct or reservoir.

The peripheral zone 16 is also integral with the central zone 12 and tear zone 14 in that it is also preferably machined or molded from the same piece of polymer material. The peripheral zone 16 has a radius of curvature of between about 4 to 20 millimeters. The radial width of the ring defined by the peripheral zone 16 is between about 0.2 to 12 millimeters. The preferred ranges are 8 to 15 millimeters for the radius of curvature and 0.5 to 6 millimeters for the radial thickness. Preferably, the radius of curvature for the peripheral zone 16 will be greater than the radius of curvature for the central zone. In addition, it is also preferred that the lateral thickness of the peripheral zone 16 be greater than the thickness of the tear zone 14. In an exemplary lens the lateral thickness of the central zone 12 is 0.5 millimeters, the tear zone 14 lateral thickness is 0.25 millimeters, and the peripheral zone 16 lateral thickness is 0.5 millimeters.

The lens 10 can be made according to any of the known machining or molding processes which allow variable radii of curvature lenses to be formed. The preferred procedure is to machine the lens from buttons or disks as is commonly known. The materials used in making the lens 10 can be any of the conventional polymers used in oxygen permeable hard, semi-hard and soft hydrogel corneal contact lenses. These materials include a variety of silicone and fluorine substituted acrylates and the soft hydrogel or silicone lens material used in contact lenses. If desired, the three zones 12, 14 and 16 can be made from the same lens material or different lens materials. For example, a suitable lens 10 could include a hard plastic central zone 12 and peripheral zone 16 while having a semi-hard or soft tear zone 14. Additional control over corneal reshaping or molding is provided by this ability to vary the hardness of the individual zones.

A study was conducted on 20 eyes (10 patients) over a two-month period in which lenses made from a fluorine acrylate plastic shaped in accordance with the present invention were prescribed. The patient criteria was: myopia up to 6 D (diopters); no previous wearing of gas permeable hard contact lenses; keratometer readings of from 40.00 through 46.00; no more than 3 diopters of corneal cylinder; no pathology; age 15 through 40; and able to wear gas permeable hard contact lens with reasonable comfort.

For each eye, three to four lenses were made with different diopters. The first lens was one diopter flatter than the flattest keratomer reading or 50 percent of the difference between the flat C.K. (corneal keratometer reading) and the flat T.K. (temporal keratometer reading). All keratometer readings were obtained with a Bausch & Lomb keratometer. T.K. readings were obtained by having the patient look with the right eye nasally to the left horizontal "+" sign on the keratometer ring. The second, third and fourth lenses were all one diopter flatter than the preceding lens to provide gradual flattening of the cornea as the patient progressed from the first through the fourth set of lenses. The last lens in the series became a retainer lens to maintain the new cornea shape.

All of the patients in this study showed reshaping of the cornea and reduction in myopia. In other studies, the best results were achieved with the patients who had never worn hard contact lenses and who had a moderate amount of corneal curvature (42 through 44). Steeper (46–49) and flatter (36–39) corneas are not as easily reshaped due to their structure.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A corneal contact lens comprising:
   a central zone having a central zone radius of curvature and a central zone lateral thickness;
   a tear zone located concentrically around said central zone, said tear zone being integral with said central zone and having a tear zone radius of curvature and a tear zone lateral thickness wherein said tear zone radius of curvature is smaller than said central zone radius of curvature; and
   a peripheral zone located concentrically around said tear zone, said peripheral zone being integral with said tear zone and having a peripheral zone radius of curvature and a peripheral zone lateral thickness wherein said peripheral zone radius of curvature is greater than or equal to said central zone radius of curvature and wherein said central zone and said peripheral zone each have a lateral thickness which is greater than the lateral thickness of said tear zone.

2. A corneal contact lens according to claim 1 wherein said central zone radius of curvature is between about 4 to 20 millimeters.

3. A corneal contact lens according to claim 2 wherein said tear zone radius of curvature is between about 0.1 12 millimeters.

4. A corneal contact lens according to claim 3 wherein said peripheral zone radius of curvature is between about 4 to 20 millimeters.

5. A corneal contact lens according to claim 1 wherein said central zone has a diameter of between about 2 to 12 millimeters.

6. A corneal contact lens according to claim 5 wherein said tear zone defines a tear ring having a radial thickness of between about 0.2 to 10 millimeters.

7. A corneal contact lens according to claim 6 wherein said peripheral zone defines a peripheral ring having a radial thickness of between about 0.2 to 12 millimeters.

8. A corneal contact lens according to claim 4 wherein said central zone has a diameter of between about 2 to 12 millimeters.

9. A corneal contact lens according to claim 8 wherein said tear zone defines a tear ring having a radial thickness of between about 0.2 to 10 millimeters.

10. A corneal contact lens according to claim 9 wherein said peripheral zone defines a peripheral ring having a radial thickness of between about 0.2 to 12 millimeters.

11. A corneal contact lens according to claim 1 wherein said lens is made from an oxygen permeable semi-hard or hard plastic.

12. A corneal contact lens according to claim 1 wherein said lens is made from a soft hydrogel plastic.

13. A corneal contact lens according to claim 1 wherein said lens is made from soft silicone polymer.

14. A corneal contact lens according to claim 1 which includes a central zone made from hard or semi-hard plastic and a tear zone made from a soft polymer.

15. A corneal contact lens according to claim 14 further including a peripheral zone made from a soft polymer.

16. A method for treating a myopic eye having a cornea with a given shape, wherein said method comprises the step of wearing a lens on the cornea of said eye for a sufficient time to alter the shape of said cornea, said lens comprising:

a central zone having a central zone radius of curvature and a central zone lateral thickness;
a tear zone located concentrically around said central zone, said tear zone being integral with said central zone and having a tear zone radius of curvature and a tear zone lateral thickness wherein said tear zone radius of curvature is smaller than said central zone radius of curvature; and
a peripheral zone located concentrically around said tear zone, said peripheral zone being integral with said tear zone and having a peripheral zone radius of curvature and a peripheral zone lateral thickness wherein said peripheral zone radius of curvature is greater than or equal to said central zone radius of curvature and wherein said central zone and said peripheral zone each have a lateral thickness which is greater than the lateral thickness of said tear zone.

* * * * *

REEXAMINATION CERTIFICATE (4129th)

United States Patent [19]
Stoyan

[11] B1 4,952,045
[45] Certificate Issued Aug. 8, 2000

[54] CORNEAL CONTACT LENS AND METHOD FOR TREATING MYOPEA

[75] Inventor: Nick Stoyan, Encino, Calif.

[73] Assignee: Contex, Inc., Sherman Oaks, Calif.

Reexamination Request:
No. 90/004,325, Aug. 5, 1996

Reexamination Certificate for:
Patent No.: 4,952,045
Issued: Aug. 28, 1990
Appl. No.: 07/357,365
Filed: May 26, 1989

[51] Int. Cl.⁷ ........................................... G02C 7/04
[52] U.S. Cl. ........................ 351/160 R; 351/160 H; 351/177
[58] Field of Search ................ 351/160 R, 160 H, 351/161, 162, 177

[56] References Cited

U.S. PATENT DOCUMENTS 4,166,255  8/1979  Graham ............................... 351/160 H

OTHER PUBLICATIONS

Fontana, Alfred A. "Orthokeratology Using The One Piece Bifocal" Orthokeratology, vol. 2, 1974, pp. 22–24.

Fontana, Alfred A. "Orthokeratology" Orthokeratology, vol. 3, 1976, pp. 81–83.

*Primary Examiner*—Scott J. Sugarman

[57] ABSTRACT

A corneal contact lens for use in treating myopia by controlled corneal molding. The lens includes a central zone having a central zone radius of curvature and a tear zone located concentrically around the central zone. The tear zone is integral with the central zone and has a radius of curvature which is smaller than the central zone. The lens may also include a peripheral zone located concentrically around the tear zone wherein the peripheral zone has a radius of curvature equal to or greater than the central zone.

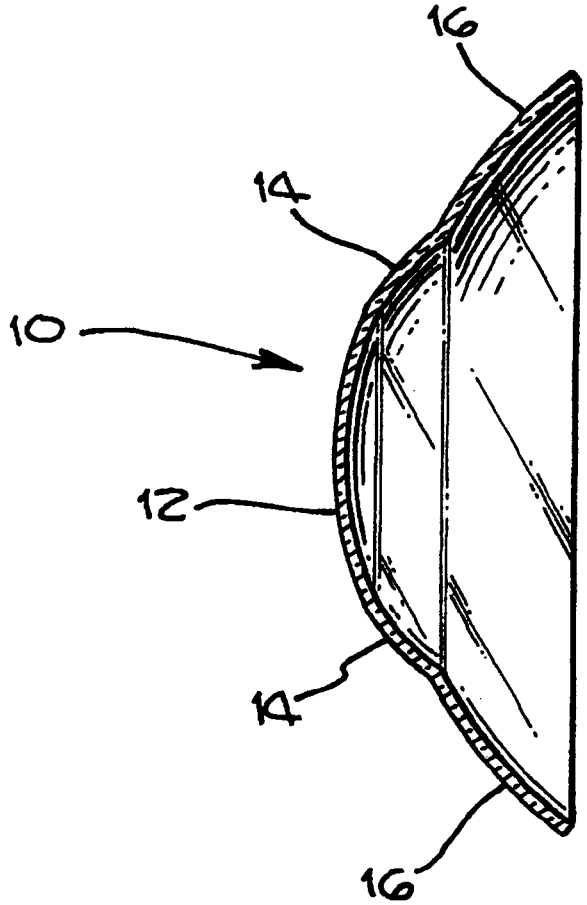

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–6 is confirmed.

* * * * *